US00PP31471P2

(12) United States Plant Patent
Stoppel

(10) Patent No.: US PP31,471 P2
(45) Date of Patent: Feb. 25, 2020

(54) ***PRUNUS* TREE NAMED 'FINAL 113'**

(50) Latin Name: ***Prunus avium* L.**
Varietal Denomination: Final 113

(71) Applicant: Peter Stoppel, Kressbronn (DE)

(72) Inventor: Peter Stoppel, Kressbronn (DE)

(73) Assignee: Peter Stoppel, Kressbronn (DE)

( * ) Notice: Subject to any disclaimer, the term of this patent is extended or adjusted under 35 U.S.C. 154(b) by 0 days.

(21) Appl. No.: 16/501,386

(22) Filed: Apr. 4, 2019

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
CPC ..... A01H 5/08; A01H 6/74
See application file for complete search history.

*Primary Examiner* — Annette H Para
(74) *Attorney, Agent, or Firm* — Myers Bigel, P.A.

(57) ABSTRACT

'Final 113' is a new cultivar of *Prunus avium* having a strong and upright tree habit, self-fertile flowers, S-alleles S3S4, a late fruit ripening time, as well as heart-shaped fruit with less cracking compared to its male parent 'Sweetheart'.

2 Drawing Sheets

Latin name of the genus and species: The Latin name of the novel plant variety disclosed herein is *Prunus avium* L.

Variety denomination: The inventive *Prunus avium* tree disclosed herein has been given the varietal denomination 'Final 113'.

BACKGROUND OF THE INVENTION

The present invention comprises a new and distinct *Prunus avium* cultivar hereinafter referred to by the cultivar name 'Final 113'. This new *Prunus* cultivar was developed through a breeding program in Baden Wuerttemberg, Germany with the goal of producing good quality fruit with a late ripening time. 'Final 113' was selected from a population of seedlings grown from a controlled cross of *Prunus avium* 'Späte von Wedler' (unpatented, female parent) x *Prunus avium* 'Sweetheart' (unpatented, male parent). The first asexual propagation of 'Final 113' was carried out in 2006 by hardwood cuttings in Germany and has been asexually reproduced repeatedly by hardwood cuttings since then. 'Final 113' has been found to retain its distinctive characteristics through successive asexual propagations.

SUMMARY OF THE INVENTION

The following are the unique combination of characteristics of this new cultivar when grown under standard horticultural practices in Germany.

1. 'Final 113' has less cracking of the fruit than 'Sweetheart'.
2. 'Final 113' has a later fruit ripening time than 'Sweetheart'.
3. 'Final 113' has S-alleles S3S4.
4. 'Final 113' has heart-shaped fruit.
5. 'Final 113' has self-fertile flowers.
6. 'Final 113' has a strong and upright tree habit.

BRIEF DESCRIPTION OF THE DRAWINGS

This new *Prunus* cultivar is illustrated by the accompanying photographs which show the plant's fruit and foliage.

The colors shown are as true as can be reasonably obtained by conventional photographic procedures. Colors in the photographs may differ slightly from the color values cited in the detailed botanical description, which accurately describe the colors of the new *Prunus* cultivar.

DETAILED BOTANICAL DESCRIPTION

Figure 1:
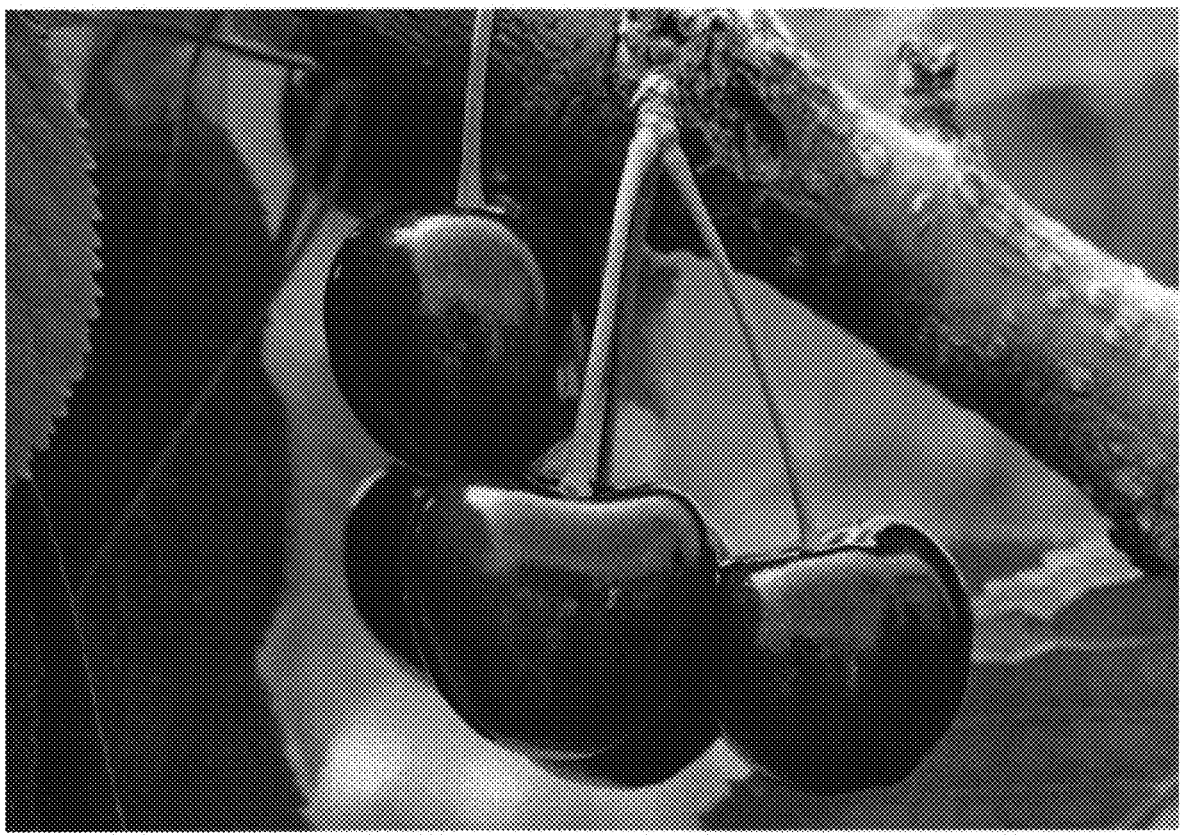
FIG. 1 is a color photograph showing the fruit on a seven-year-old tree of 'Final 113'.
Figure 2:
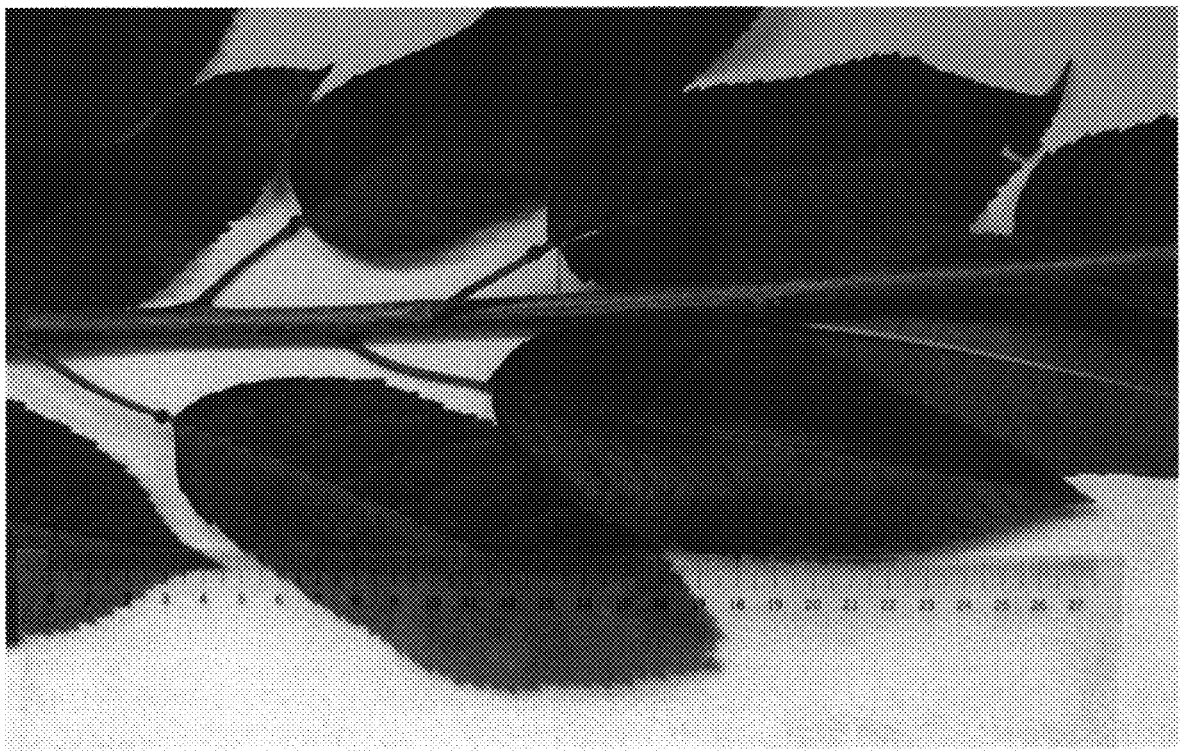
FIG. 2 is a color photograph showing the foliage (upper surface) from a seven-year-old tree of 'Final 113'.

The following is a detailed description of the botanical characteristics of the new and distinct *Prunus* cultivar known by the denomination 'Final 113'. The detailed description was taken on a seven-year-old tree in Germany. All colors cited herein refer to The Royal Horticultural Society Colour Chart (The Royal Horticultural Society (R.H.S.), London, 2005 Edition). Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name.*—*Prunus avium* 'Final 113'.

Parentage: Seedling grown from a controlled cross of *Prunus avium* 'Späte von Wedler' (unpatented, female parent) x *Prunus avium* 'Sweetheart' (unpatented, male parent).

Plant description:

*Size.*—Height about 3 m, width about 2 m (10 cm above ground).

*Vigor.*—Medium.

*Density.*—Medium.

*Form.*—Upright spread with medium level of lateral branching.

*Growth type.*—Spreading.

*Bearing*.—Annual on spurs and 3 total bud positions located at the base of one year old shoots.

Trunk:

*Size*.—Medium.

*Surface texture*.—Smooth with prominent lenticels.

*Bark color*.—Moderate olive brown 199A.

*Lenticels*.—Length: 1-2 cm. Width: 0.5 cm. Color: grayed orange 167A. Density: medium.

Branches:

*Diameter*.—1-2 cm.

*Surface texture*.—Average, typical for Sweet Cherry.

*Color*.—Brownish orange 164A.

*Form*.—Typical for Sweet Cherry.

*Average angle*.—60-75 degree.

*Bud arrangement*.—Typical for Sweet Cherry.

*Lenticels*.—Length: about 1 mm. Width: about 1 mm. Shape: roundish. Density: few, scattered. Color: grayed yellow 161A.

Leaves:

*Length*.—17-19 cm.

*Width*.—7-9 cm.

*Form*.—Round, pointed.

*Texture*.—Leathery, crisp feeling.

*Thickness*.—Medium.

*Base*.—Pointed.

*Apex*.—Pointed.

*Margin*.—Serrations irregular.

*Color*.—Mature leaves: Upper surface: strong yellowish green 143A. Lower surface: light yellowish green 142D.

*Petiole*.—Shape: narrow. Length: 3-4 cm. Diameter: about 2 mm. Color: adaxial: dark red 59A; abaxial: brilliant yellowish green 149C.

*Veins*.—Venation type: pinnate. Color: Upper surface: light yellowish green 154D.

Flower buds:

*Pedicel*.—Length: 12 mm. Diameter: 0.4 mm.

*Bud*.—Length: about 1 cm. Width: under 1 cm. Color: reddish.

Flowers:

*Bloom timing*.—21.04. Kressbronn, Germany.

*Blooming period*.—Medium-early season, with Burlat.

*Pollination requirements*.—Self-fertile.

*Number of flowers per raceme*.—3 to 7.

*Petals*.—Number: 5. Length: 17 mm. Width: 13 mm. Shape: round. Apex: slightly obcordate. Margin: slightly undulated. Texture and appearance: soft texture.

*Color*.—Fully opened: Upper surface: White 155D. Lower surface: White 155D.

*Sepals*.—Shape: conical. Margin: regular. Length: 5-7 mm. Width: about 5 mm. Color: Upper surface: Green 143C. Lower surface: Green 143C.

*Stamens*.—Number (per flower): 4-5. Filament length: 13 mm Width: 0.1 mm.

*Anthers*.—Shape: kidney. Length: 0.6 mm. Color: yellow 13B.

*Pollen*.—Color: yellow 13B. Amount (generally): plentiful.

*Pistils*.—Length: 12 mm.

*Style*.—Length: 4-6 mm. Color: green 143C

*Stigma*.—Shape: oval. Color: green 144A.

Fruit:

*Maturity when described*.—30.07.16 (12 days after Regina in south Germany).

*Size*.—Diameter: 3 cm. Length: 3.2 cm.

*Skin*.—Thickness: medium. Texture: medium. Tendency to crack: not prone to cracking from rain. Color: dark red 53A.

*Flesh*.—Aroma: pleasant. Color: dark red 53A. Texture: very firm. Eating quality: good.

*Seeds*.—Number per fruit: 1. Length: 1.3 cm. Breadth: 0.7-0.9 cm. Form: round. Color: light brown 160B.

*Stem*.—Length: 5.5 cm. Width: 0.1 cm. Color: light green 145A.

COMPARISON OF 'FINAL 113' WITH COMMERCIAL CULTIVARS AND PARENTAL PLANTS

'Final 113' is similar to its male parent, 'Sweetheart', in that both have S-alleles S3S4 and both are self-fertile. 'Final 113' is distinct from 'Sweetheart' by its stronger, upright tree habit compared to the weaker and broad tree habit of 'Sweetheart'. In addition, the fruit shape of 'Final 113' is heart-shaped compared to the round fruit shape of 'Sweetheart' and 'Final 113' has less fruit cracking than 'Sweetheart'. In addition, 'Final 113' has a larger fruit size than 'Sweetheart'.

'Final 113' is distinct from the *Prunus* cultivar 'Tieton' (U.S. Pat. No. 11,385), by its S-alleles which are S3S4 compared to S-alleles S3S9 in 'Teiton'. 'Final 113' is 13 days later in ripening than 'Regina' (not patented). The fruit shape of 'Final 113' is heart-shaped compared to 'Regina', which has a more round-shaped fruit. 'Final 113' has firmer fruits than 'Regina'. Flowering in 'Final 113' is medium-early compared to 'Regina', which is very late.

What is claimed is:

1. A new and distinct *Prunus* tree named 'Final 113' substantially as illustrated and described herein.

* * * * *